United States Patent [19]

Glasheen

[11] Patent Number: 4,592,096
[45] Date of Patent: Jun. 3, 1986

[54] LATCH FOR MOUNTING A GOGGLE SYSTEM TO A FACE MASK

[75] Inventor: W. Michael Glasheen, North Reading, Mass.

[73] Assignee: Baird Corporation, Bedford, Mass.

[21] Appl. No.: 627,960

[22] Filed: Jul. 5, 1984

[51] Int. Cl.⁴ .............................................. A61F 9/02
[52] U.S. Cl. .......................................... 2/427; 2/453; 350/547; 350/145
[58] Field of Search ................... 2/427, 453, 6, 9, 422, 2/10; 350/547, 548, 549, 145, 146; 250/213 VT; 24/580, 581, 584; 403/321, 322, 325, 326, 330

[56] References Cited

U.S. PATENT DOCUMENTS 2,935,910 5/1960 Schmidt ............................. 350/146
4,449,787 5/1984 Burbo et al. ................... 350/548 X
4,463,252 7/1984 Brennan et al. ............. 250/213 VT

FOREIGN PATENT DOCUMENTS 0196554 3/1958 Austria .................................. 2/453

Primary Examiner—Peter Nerbun
Attorney, Agent, or Firm—Morse, Altman & Dacey

[57] ABSTRACT

An improved latch to mount a night vision goggle system to a face mask is disclosed. The latch comprises a part secured to the face mask and parts secured to the goggle system. Specifically, it includes a tongue, which angularly adjustably is secured to the face mask. In one embodiment, the goggle system is provided with a receiver, a switch to render the system operational mounted adjacent the receiver and means mounted in operative association with the receiver both releasably to secure the goggle system to the face mask via the tongue and also to actuate the switch. In a second embodiment, the goggle system is provided with a receiver and a leaf spring releasably to secure the goggle system to the face mask via the tongue.

9 Claims, 5 Drawing Figures

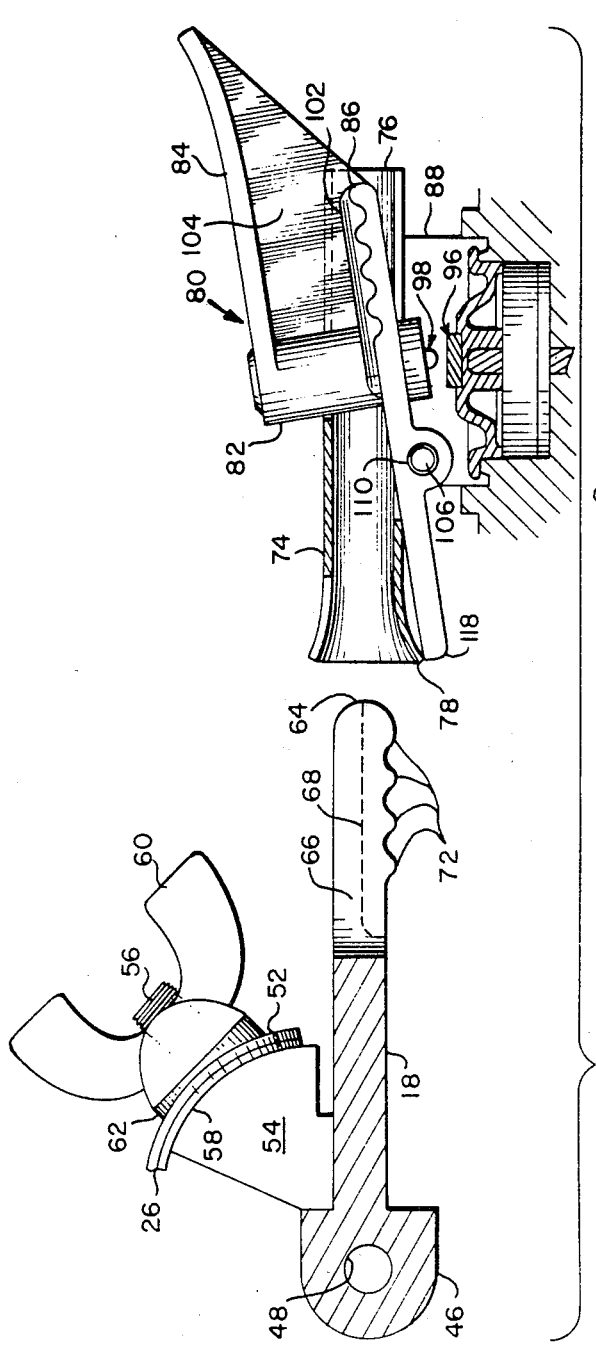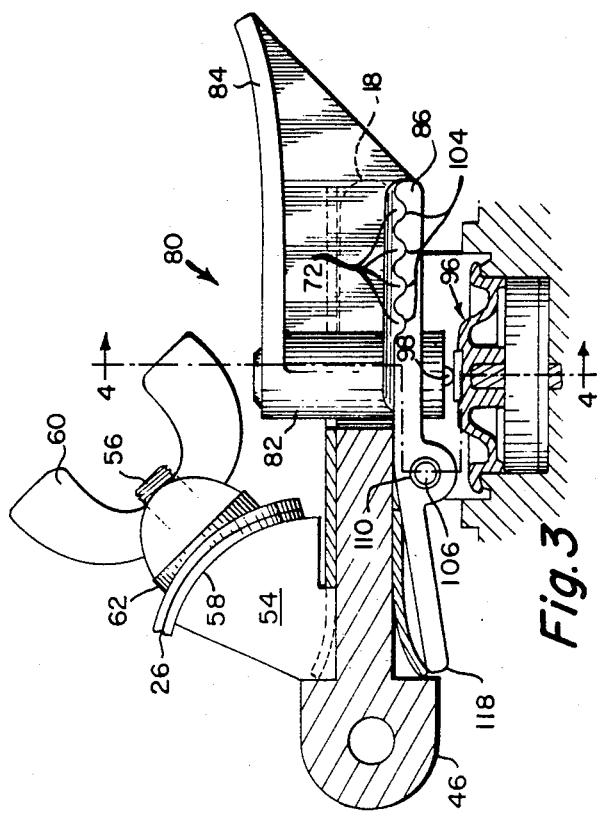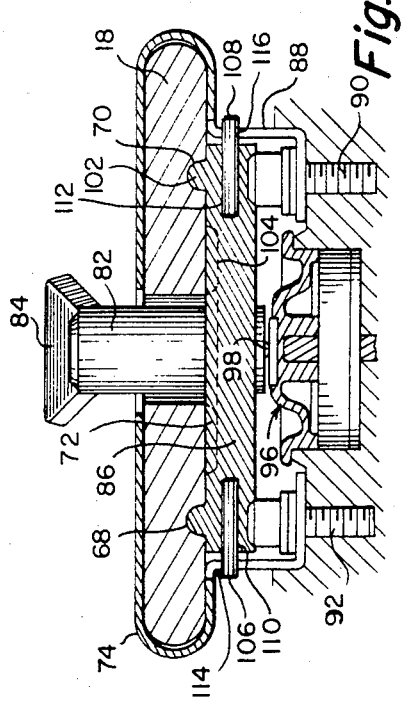

LATCH FOR MOUNTING A GOGGLE SYSTEM TO A FACE MASK

BACKGROUND OF THE INVENTION

1. Field of the Invention

The present invention relates generally to mounting night vision goggles to face masks and, more particularly, to an improved latch to mount a night vision goggle system to a face mask.

2. The Prior Art

Night vision goggles are binocular viewers that operate at very low light levels to allow the user to see, move and perform some tasks in the dark. They are normally worn attached to a face mask so as to free the user's hands.

There are various known ways of attaching the goggles to the face mask. One is disclosed in an application Ser. No. 337,023, filed Jan. 4, 1982, entitled NIGHT VISION GOGGLE SYSTEM, now U.S. Pat. No. 4,463,252 (it's been allowed on 2/23/84) and assigned to a common assignee, the Baird Corporation of Bedford, Massachusetts, the disclosure of which is incorporated herein by reference. In the disclosure of said application, the goggle system is head mounted via a quick-release connection to a face mask provided with an adjustable strap assembly. Although the quick-release connection is satisfactory, it nevertheless lacks certain desirable attributes, including features of being up and down, i.e., angularly adjustable, of rendering the goggles operational when connected, and of being capable of one-handed attachment. There is thus both room and want for improvement as regards mounting night vision goggle systems to face masks

SUMMARY OF THE INVENTION

It is a principal object of the present invention to overcome the above disadvantages by providing an improved latch to mount a night vision goggle system to a face mask.

More specifically, it is an object of the present invention to provide an improved latch to mount a night vision goggle system to a face mask characterized by, among others, one-handed operation and by up and down adjustability. It is a further object of the present invention to provide an improved latch to mount a night vision goggle system to a face mask essentially comprising a tongue angularly adjustably secured to the face mask and receiver means adapted to be engaged by and be fastened to the tongue and secured to the goggle system. Preferably, the tongue is secured to the face mask by a pair of wires formed of a horizontal and a pair of vertical sections. The pair of wires in the horizontal section are offset at least vertically so as to define a top and a bottom wire. Preferably, the tongue is secured cantilever style about the bottom wire and is angularly adjustably secured to the pair of wires by a member secured to the top wire. The member is operatively connected to the tongue. Preferably and to facilitate the proper lateral alignment of the goggle system to the face mask, the tongue is provided with a pair of alignment grooves to cooperate with a pair of ribs in the receiver means. The tongue further is provided with a plurality of detents designed to cooperate with a plurality of indents formed in the receiver means, whereby the depth of penetration of the tongue can be varied. Preferably, the receiver means comprises a receiver, an actuator operable manually and/or by the tongue entering the receiver, and a bracket formed on the underside of the receiver by means of which the receiver means is secured to the goggle system. Preferably, the goggle system is provided with a switch to render the system operational and mounted in operative association with the actuator.

Other objects of the present invention will in part be obvious and will in part appear hereinafter.

The invention accordingly comprises the improved latch of the present disclosure, its components, parts and their interrelationships, the scope of which will be indicated in the appended claims.

BRIEF DESCRIPTION OF THE DRAWINGS

For a fuller understanding of the nature and objects of the present invention, reference is to be made to the following detailed description, which is to be taken in connection with the accompanying drawings, wherein:

FIG. 2 is a side elevation, partly in section, of certain parts of the improved latch of FIG. 1 but on an enlarged scale;

FIG. 3 is a view similar to FIG. 2 but showing the parts in a different relation to one another;

FIG. 4 is a section, partly in elevation, along the line 4—4 of FIG. 3; and

DETAILED DESCRIPTION OF THE PREFERRED EMBODIMENTS

Figure 1:
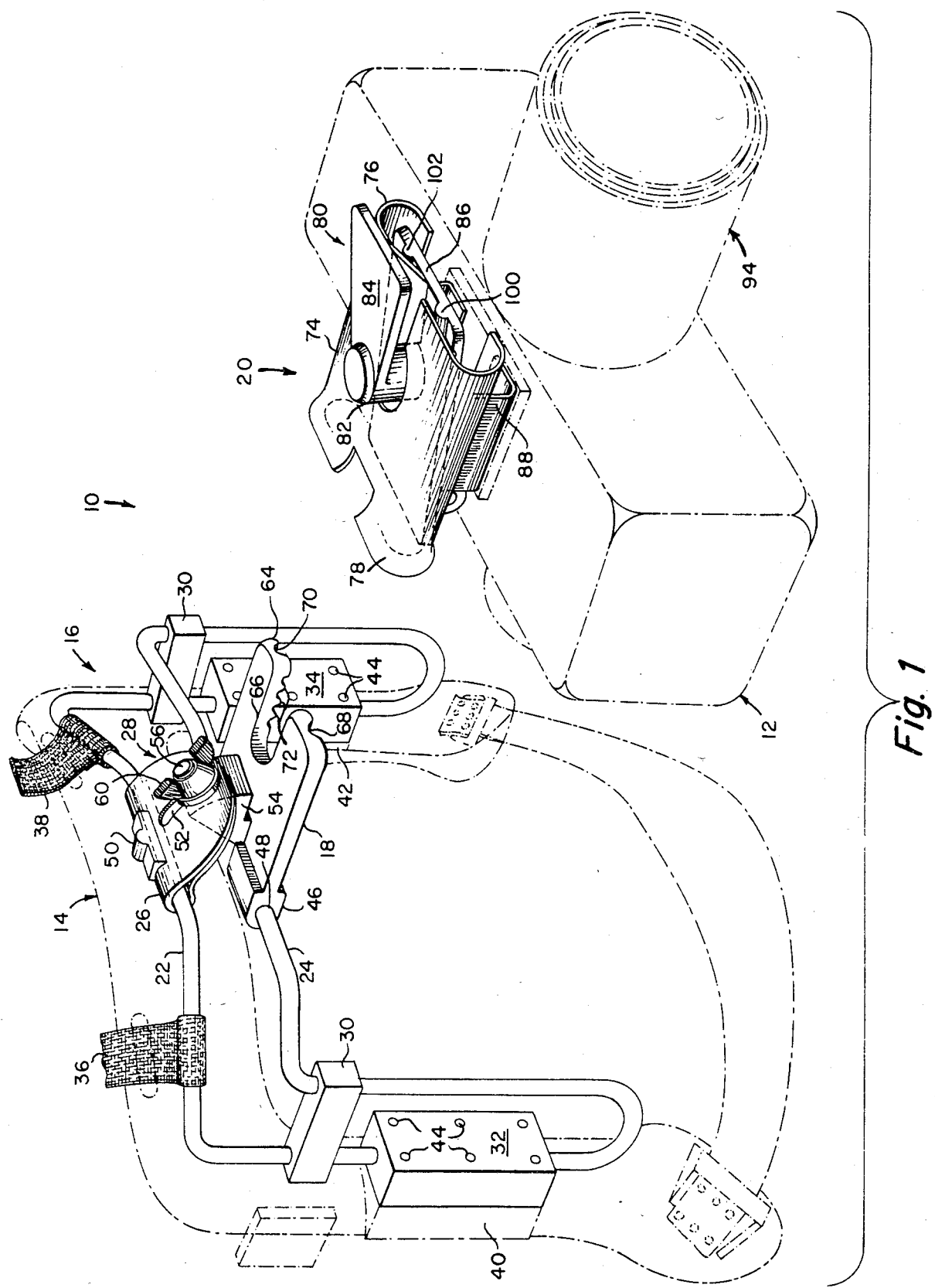
FIG. 1 is a perspective view of an improved latch constructed in accordance with the present invention and showing a part thereof secured to a face mask and parts secured to a night vision goggle system.

In general, the present invention provides an improved latch 10 to mount a night vision goggle system 12 to a face mask 14. Night vision goggle systems are binocular viewers that operate at low light levels to allow the user to see, move and perform some tasks, including map reading, light repair and vehicular driving, in the dark.

As mentioned, a night vision goggle system and one way of its attachment to a face mask are disclosed in said U.S. application Ser. No. 337,023, entitled NIGHT VISION GOGGLE SYSTEM. The quick-release connection therein disclosed lacks certain desirable features, such as up and down adjustability, one handed attachment and detachment, and the capability of rendering the goggles operational when they are being attached to the face mask, to mention some.

The improved latch 10 of the invention essentially comprises mounting means 16 secured to the face mask 14, a tongue 18 angularly adjustably secured to the mounting means 16 and receiving means 20 for the tongue 18 and secured to the night vision goggle system 12.

In the preferred embodiment illustrated in FIGS. 1-4, the mounting means 16 angularly adjustably securing the tongue 18 to the face mask 14 comprises a pair of wires 22 and 24, a member 26 secured about the top wire 22, and means 28 operatively connecting the member 26 to the tongue 18. Preferably, the pair of wires 22 and 24 are formed of a single wire that has been deformed into the shape shown, including a central horizontal section and a pair of side vertical sections. Dividers 30, 30 keep the pair of wires 22 and 24 in parallel spaced relation, particularly along the side vertical sections. The pair of wires 22 and 24 are, however, bent somewhat forward at the central horizontal section, with the top wire 22 being bent forward more than the bottom wire 24 so as to position the pair of wires 22 and 24 substantially above one another in the same vertical plane. The pair of wires 22 and 24 preferably are secured to the face mask 14, first by a pair of solid members 32 and 34 and second, by a pair of flexible straps 36 and 38. The solid members 32 and 34 are conveniently secured to a pair of backup parts 40 and 42 by a plurality of screws 44. The backup parts 40 and 42 themselves in turn are secured to the face mask 14 as, for example, by being glued and/or sewed thereto. The face mask 14 itself can be identical with the one disclosed in said U.S. application Ser. No. 337,023 or it can be of other known design.

The tongue 18 is somewhat thicker at its distal end 46, which end 46 is provided with a transverse bore 48, designed to accommodate therein the bottom wire 24. The diameter of the bore 48 is slightly larger than the diameter of the wire 24 so as to be able freely to rotate thereabout. The member 26, in contrast, is rigidly mounted, as by a clamp 50 or the like, against rotational displacement about the top wire 22. The member 26 is provided with a slot 52, which extends from the vicinity of the wire 22 forward, substantially along the length of the member 26.

The means 28 operatively connecting the member 26 to the tongue 18 comprises a part 54 secured, as for example by welding, to the tongue 18 centrally and near the distal end 46 thereof. The part is provided with an integrally formed and externally threaded stud 56 designed to extend through the slot 52 of the member 26. As may be best observed in FIG. 2, the part 54 presents an arcuate surface 58, and the member 26 is shaped to follow that surface 58. It will be evident that the part 54, and thereby the tongue 18, can be angularly displaced along the underside of the member 26 and along the full length of the slot 52. With the desired angular position selected for the tongue 18, the part 54 and thereby the tongue 18 are all secured in that angular position by a wing nut 60. Preferably, a suitable washer 62 (observe FIG. 2) is interposed between the wing nut 60 and the member 26.

The frontal free end 64 of the tongue 18 is provided with a central U-shaped cutout 66. On the underside of the tongue 18, a pair of parallel alignment grooves 68 and 70 are formed lengthwise of the tongue 18, and a plurality of parallel spaced detents 72 crosswise of the tongue 18.

The receiving means 20 for the tongue 18, mounted on the night vision goggle system 12, comprises a receiver 74 having a front end 76 and a flared rear end 78, an actuator 80 formed of a hub 82 and of a pair of flat portions connected to the hub 82, and a bracket 88 integrally formed on or secured to the underside of the receiver 74. It is with the aid of this bracket 88 that the receiving means 20 is secured, as by a pair of screws 90 and 92 (observe FIG. 4), to the center topside of the night vision goggle system 12 and in optical alignment with the objective lens assembly 94 thereof. Preferably and in operative association with the acutator 80, the goggle system 12 is provided with a switch 96 designed to render the goggle system 12 operational by activating its battery. Normally, such a swirch is mounted on one side of the goggle system, as in said U.S. application Ser. No. 337,023, and is manually operable.

The hub 82 of the actuator 80 houses a spring-loaded ball plunger 98, which in one position shown in FIG. 2 is in close proximity to, but not touching, the switch 96. When the actuator 80 is moved downwardly into its second position shown in FIGS. 3 and 4, whether manually as by pushing down on the top flat portion 84 or via the action of the tongue 18 as illustrated in FIGS. 3 and 4, the spring loaded ball plunger 98 first contacts and then depresses the switch 96. It is pointed out that the goggle system 12 is and remains operational only while the plunger 98 keeps the switch 96 depressed, providing thereby a "dead-man switch" capability.

To assure precise lateral alignment with the objective optical axis of the goggle system 12, the bottom flat portion 86 is provided with a pair parallel spaced ribs 100 and 102 designed to fit into and to cooperate with the pair of alignment grooves 68 and 70 formed in the underside of the tongue 18. The bottom flat portion 86 further is provided with one or more transverse indents 104 designed to cooperate with the plurality of detents 72 formed on the underside of the tongue 18, whereby the tongue 18 can be secured depthwise variably within the receiver 74.

Preferably, the actuator 80 is operatively mounted within and to the receiving means 20 via a pair of pins 106 and 108 disposed within a pair of transverse grooves 110 and 112 formed in the bottom flat portion 86 about midway thereof, and with the pins extending through a pair of holes 114 and 116 formed in the bracket 88.

As is evident from viewing FIGS. 2-4, when the tongue 18 enters the receiver 74, its front end 64 is guided by the cooperation of the pair of alignment grooves 68 and 70 with the pair of ribs 100 and 102 to slide along the bottom flat portion 86 of the actuator 80, thereby depressing the same about the pivot pins 106 and 108. The depressing action imparted to the bottom flat portion 86 by the tongue 18 is transmitted thereby to the hub 82, whose spring-loaded ball plunger 98 first contacts and then depresses the switch 96. As long as the tongue 18 remains within the receiver 74, as illustrated in FIGS. 3 and 4, the switch 96 remains actuated and the goggle system 12 remains operational. The moment the tongue 18 is withdrawn from the receiver 74, the ball 98 is caused to move away from the switch 96 by the spring action thereof into the normal position shown in FIGS. 1 and 2. With the switch 96 disengaged, the goggle system 12 is once again rendered inoperative. Of course, the operator can render the goggle system 12 operational simply by manually depressing, and holding down, the top flat portion 84 of the actuator 80.

Figure 5:
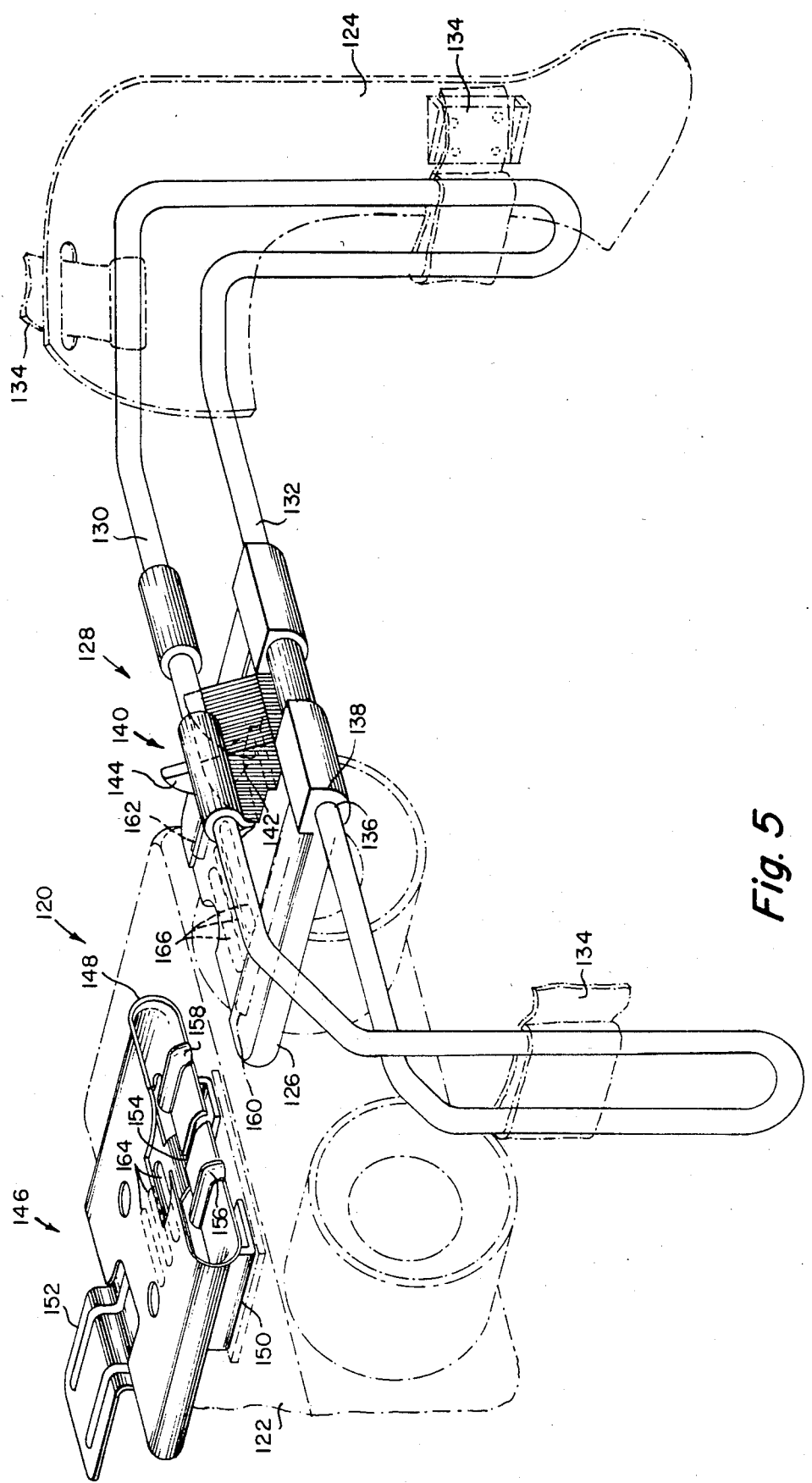
FIG. 5 is perspective view of another embodiment of an improved latch constructed in accordance with the present invention.

In FIG. 5 there is illustrated a second preferred embodiment of an improved latch 120 to mount a night vision goggle system 122 to a face mask 124. The latch 120 comprises a tongue 126 angularly adjustably secured, via a mounting means 128, to the face mask 124. The mounting means 128 comprises a pair of wires 130 and 132 preferably secured to the face mask 124 by a plurality of flexible straps 134. The pair of wires 130 and 132 preferably are formed of a single wire into a central horizontal section and two vertical side sections. Just like the pair of wires 22 and 24 in FIG. 1, the pair of wires 130 and 132 in the central horizontal section also are being offset from one another vertically in the same vertical plane.

The tongue 126 also is mounted cantilever style about the bottom wire 132, extending through a transverse bore 136 formed in one end 138 thereof. A member 140 is, however, loosely mounted about the top wire 130, and is operatively connected to the tongue 126 via a stud 142 and a wing nut 144. In this embodiment, both the member 140 and the thereto connected tongue 126 move in unison angularly until they are secured, by the tightening of the wing nut 144.

The goggle system 122 also is provided with receiving means 146 comprising a receiver 148, a bracket 150 by means of which the receiver 148 is secured to the goggle system 122, and a leaf spring 152 secured to and within the receiver 148 as at 154, as for example by being spot welded thereto. The receiver 148 further is provided with a pair of raised ribs 156 and 158, which are designed to cooperate with a pair of parallel spaced alignment grooves 160 and 162 formed in the underside of the tongue 126. The leaf spring 152 further is provided with a plurality of transverse indents 164 to secure the tongue 126 depthwise variably within the receiver 148. The goggle system 122, once connected to the tongue 126, can be easily disconnected therefrom by simply depressing the leaf spring 152 and pulling forward on the goggle system 122, in the same way as depressing the top flat portion 84 and withdrawing forward the goggle system 12 of FIG. 1. The underside of the tongue 126 preferably also is provided with a plurality of transverse detents 166 cooperatively to engage the plurality of indents 164.

Preferably, the operative parts of the latches 10 and 120 such as the tongue 18 and/or 126, and the receiving means 20 and/or 146, formed of a suitable metal, such as for example, stainless steel.

Thus, it has been shown and described an improved latch 10 to mount a night vision goggle system to a face mask, which latch 10 satisfies the objects and advantages set forth above.

Since certain changes may be made in the present disclosure without departing from the scope of the present invention, it is intended that all matter described in the foregoing specification or shown in the accompanying drawings, be interpreted in an illustrative and not in a limiting sense.

What is claimed is:

1. A latch to mount a goggle system to a face mask comprising:
    (a) mounting means secured to said face mask;
    (b) a tongue angularly adjustably secured to said mounting means; and
    (c) receiving means for said tongue secured to said goggle system, including means for securing said tongue within said receiving means;
    (d) said mounting means comprising a pair of wires formed of horizontal and vertical sections, said pair of wires in said horizontal section being offset vertically so as to form a top and a bottom wire, a member secured about said top wire and operatively connected to said tongue to secure said tongue angularly adjustably about said horizontal section.

2. The latch of claim 1 wherein said member is provided with an arcuate slot and said tongue with a stud to extend through said slot, and a wing nut for securing said stud, and thereby said tongue, in a position along the length of said arcuate slot.

3. The latch of claim 1 wherein said tongue has a front and a rear, and is formed with a U-shaped cutout at said front and a transverse bore at said rear, said tongue being further provided with a pair of parallel spaced alignment grooves.

4. A latch to mount a goggle system to a face mask comprising:
    (a) mounting means secured to said face mask;
    (b) a tongue angularly adjustably secured to said mounting means; and
    (c) receiving means for said tongue secured to said goggle system, including means for securing said tongue within said receiving means;
    (d) said receiving means for said tongue comprising a receiver having a front end and a flared rear end, an actuator formed of a hub and a pair of flat portions operatively connected to said hub, one of said flat portions designed for manual actuation and the other of said flat portions designed for actuation by said tongue upon entering said receiver.

5. The latch of claim 4 wherein said goggle system is further provided with a switch to render said system operational, and wherein said hub is a spring-loaded ball plunger mounted in operative association with said switch, whereby downward displacement of said ball plunger effected by the actuation of one of said pair of flat portions actuates said switch.

6. The latch of claim 4 wherein said means for receiving said tongue within said receiving means includes a plurality of detents formed on said tongue and at least one indent formed on one of said pair of flat portions to cooperate with said plurality of detents, whereby said tongue can be secured depthwise variably within said receiving means.

7. The latch of claim 5 wherein said receiving means is secured to said goggle system with a pair of screws.

8. The latch of claim 4 further including a bracket formed on the underside of said receiver, wherein said one of said pair of flat portions designed for actuation by said tongue is secured to said bracket.

9. The latch of claim 8 further including a transverse groove formed midway in said one of said pair of flat portions designed for actuation by said tongue and a pin designed to fit within said transverse groove so as to flexibly mount the same to said bracket.

* * * * *